United States Patent [19]

Tosaka et al.

[11] 4,275,157

[45] Jun. 23, 1981

[54] METHOD FOR THE PRODUCTION OF L-LYSINE

[75] Inventors: Osamu Tosaka, Tokyo; Eiji Ono, Kawasaki; Masaru Ishihara, Yokohama; Hajimu Morioka, Kawasaki; Koichi Takinami, Yokohama, all of Japan

[73] Assignee: Ajinomoto Company, Incorporated, Tokyo, Japan

[21] Appl. No.: 56,414

[22] Filed: Jul. 10, 1979

[30] Foreign Application Priority Data

Jul. 10, 1978 [JP] Japan .................................. 53-83807

[51] Int. Cl.³ ............................................. C12P 13/08

[52] U.S. Cl. .................................. 435/115; 435/172; 435/840; 435/843

[58] Field of Search ......................................... 435/115

[56] References Cited

U.S. PATENT DOCUMENTS

| 3,756,916 | 9/1973 | Leavitt | 435/115 |
| 3,871,960 | 3/1975 | Kubota et al. | 435/115 |

Primary Examiner—Alvin E. Tanenholtz
Attorney, Agent, or Firm—Oblon, Fisher, Spivak, McClelland & Maier

[57] ABSTRACT

L-lysine is produced by culturing mutants of Corynebacterium or Brevibacterium which are sensitive to fluoropyruvic acid.

4 Claims, No Drawings

METHOD FOR THE PRODUCTION OF L-LYSINE

This invention relates to a method for producing L-lysine by fermentation.

L-Lysine, which is used as a feed stuff, has been produced by fermentation process.

The inventors have found that when sensitivity to fluoropyruvic acid is given to known L-lysine producing microorganisms of the genus Corynebacterium or Brevibacterium, the productivity of L-lysine is significantly increased.

The microorganisms used in the process of this invention are the mutants which belong to the genus Brevibacterium or Corynebacterium, have the characteristics known as necessary for the production of L-lysine such as homoserine-requirement and resistance to S-(2-aminoethyl)-L-cysteine (hereinafter referred to as AEC), and further have the sensitivity to fluoropyruvic acid.

The mutants as above can be induced from the parents strains by conventional mutation manners such as exposing to UV-rays and to N-methyl-N'nitro-N-nitrosoguanidine.

The parents strains are, for example, *Brevibacterium divaricatum* ATCC 14020, *Brevibacterium flavum* ATCC 14067, *Brevibacterium lactofermentum* ATCC 13869, *Brevibacterium roseum* 13825, *Corynebacterium acetoacidophilum* ATCC 13870, and *Corynebacterium lilium* ATCC 15990. Those parents strains have the common characteristics that their mutants strains can produce L-lysine.

The mutants sensitive to fluoropyruvic acid grow more poorly than their parent strains in the medium which contains fluoropyruvic acid, and then the mutants can be separated from their parents by the replication-method.

The method by which the mutants of this invention were induced and the sensitivity of the mutants to fluoropyruvic acid are shown below:

*Brevibacterium lactofermentum* AJ 11082 (FERM-P 3840; AEC$^\gamma$, CCL$^\gamma$ (CCL: α-chlorocaprolactum), Ala$^-$), NRRL B-11470 which was derived from ATCC 13869, was treated with 250 μg/ml N-methyl-N'-nitro-N-nitrosoguanidine at 30° C. for 30 minutes. Thereafter, colonies which were formed on the following agar-medium containing an amount of fluoropyruvic acid which was not inhibitive to the growth of the parent strains were picked up:

Agar-medium:
  Glucose: 2.0 g/dl
  Urea: 0.25 g/dl
  Ammonium sulfate: 1.0 g/dl
  KH$_2$PO$_4$: 0.1 g/dl
  MgSO$_4$.7H$_2$O: 0.04 g/dl
  FeSO$_4$.7H$_2$O: 1.0 mg/dl
  MnSO$_4$.4H$_2$O: 1.0 mg/dl
  Biotin: 50 μg/l
  Thiamine.HCl: 100 μg/l
  NaCl: 5.0 mg/l
  Nicotin amide: 0.5 mg/dl
  L-Alanine: 50 mg/dl
  pH 7.2

Among the mutants thus obtained, most high L-lysine producer AJ 11273 (FERM-P 4547; AEC$^\gamma$, CCL$^\gamma$, Ala$^-$, FP$^s$ (FP; fluoropyruvic acid)) NRRL B-11471 were obtained.

By the analogous manner, *Corynebacterium acetoglutamicum* AJ 11274 (FERM-P 4548; AEC$^\gamma$, Ala$^-$, FP$^s$) NRRL B-11473 was obtained from AJ 11094 (FERM-P3856; AEC$^\gamma$, Ala$^-$) NRRL B-11475 and *Brevibacterium flavum* AJ 11276 (FERM-P 4550; Hse$^-$, Ala$^-$, FP$^s$) NRRL B-11474 from AJ11275 (FERM-P 4549; Hse$^-$, Ala$^-$) NRRL B-11472.

The degree of sensitivity to fluoropyruvic acid is shown in Table 1.

TABLE 1

| FP concentration (μg/ml) | AJ11082 | Growth (O.D.) | | | | |
|---|---|---|---|---|---|---|
| | | AJ11273 | AJ11094 | AJ11274 | AJ11275 | AJ11276 |
| — | 0.300 | 0.300 | 0.300 | 0.300 | 0.300 | 0.300 |
| 0.3 | 0.306 | 0.135 | 0.310 | 0.300 | 0.300 | 0.090 |
| 1 | 0.294 | 0.120 | 0.305 | 0.150 | 0.295 | 0.060 |
| 3 | 0.084 | 0.060 | 0.120 | 0.090 | 0.095 | 0.008 |
| 10 | 0.003 | 0.003 | 0.005 | 0.005 | 0.004 | 0.003 |

O.D.: Optical density at 562mμ of 26 times dilute of the culture broth.

Each testing strains was washed with the aqueous medium mentioned below and suspended in 6 ml of the aqueous medium (the optical density at 562 mμ of 26 times dilute of the suspension was 0.330 to 0.300). The suspension (0.1 ml) was transferred into 3 ml of the aqueous medium placed in a test tube which further contained the amount of fluoropyruvic acid shown in Table 1. The cultivation was carried out at 30° C. for 24 hours with shaking.

Aqueous Medium:
  Glucose: 2 g/dl
  (NH$_4$)$_2$SO$_4$: 1.0 g/dl
  KH$_2$PO$_4$: 0.1 g/dl
  MgSO$_4$.7H$_2$O: 0.04 g/dl
  NaCl: 0.05 g/dl
  Urea: 0.25 g/dl
  Biotin: 50 μg/l
  Thiamine.HCl: 200 μg/l
  FeSO$_4$.7H$_2$O: 1.0 mg/dl
  MnSO$_4$.4H$_2$O: 1.0 mg/dl
  L-Alanine: 50 mg/dl
  Nicotine amide: 5.0 mg/dl
  pH 7.2 (with KOH)

The mutants of this invention are cultured in conventional media to produce L-lysine. The media contain carbon source, nitrogen source, inorganic ions. As the carbon source, saccharides (such as glucose and sucrose, and molasses and starch hydrolyzate containing these saccharides), organic acids (such as acetic acid and propionic acid) alcohols (such as ethanol and propanol) hydrocarbons, and so on may be used. Nitrogen sources are, for example, ammonium salts, gaseous ammonia, urea, aqueous ammonia.

Cultivation is carried out under aerobic conditions. The temperature of the medium is controlled in the range from 24° to 37° C. The cultivation is continued for 2 to 7 days preferably adjusting the pH of the medium at 5.0 to 9.0 with acids or alkalis (such as urea or gaseous ammonia).

L-Lysine accumulated in the resultant culture broth is recovered by conventional manners such as using ion exchange resine.

EXAMPLE 1

Twenty ml batches of the culture medium mentioned below were placed in 500 ml-flasks and heated to sterilize at 110° C. for 5 minutes.

Culture Medium:
 Glucose: 10 g/dl
 Ammonium sulfate: 4.5 g/dl
 $KH_2PO_4$: 0.1 g/dl
 $MgSO_4.7H_2O$: 0.04 g/dl
 $FeSO_4.7H_2O$: 1.0 mg/dl
 $MnSO_4.4H_2O$: 1.0 mg/dl
 Biotin: 50 μg/l
 Thiamine.HCl: 200 μg/l
 Soyprotein hydrolyzate (Total Nitrogen 7%): 1.5 ml/dl
 Calcium carbonate: 5.0 g/dl
 pH 7.8

Each of microorganisms listed in Table 2 which had been previously cultured on glucose-bouillon slants was inoculated in each bach of the culture medium, and cultured at 31° C. for 72 hours.

After 72 hours of the cultivation, L-lysine accumulated in the resultant culture broth were colorimetrically determined, and are shown in Table 2.

TABLE 2

| microorganisms | L-Lysine accumulated (as L-Lysine HCl) | Yield |
|---|---|---|
| AJ 11082 | 3.8 g/dl | 38% |
| AJ 11273 | 4.1 | 41 |
| AJ 11094 | 3.5 | 35 |
| AJ 11274 | 3.9 | 39 |
| AJ 11275 | 3.2 | 32 |
| AJ 11276 | 3.8 | 38 |

One liter of the culture broth of AJ 11273 obtained by the same method as above was centrifuged to remove cells and other precipitates and the supernatant was passed through the column of "Amberlite IR-120" OH type. L-Lysine absorbed on the resine was eluted with 3% ammonia water, the eluate was evaporated and added with HCl, and 34.2 g, L-lysine.HCl.2 aq christallines were obtained upon cooling.

EXAMPLE 2

Brevibacterium lactofermentum AJ 11273 and its parent AJ 11082 were each inoculated from an agar-slant to 50 ml of the following seed medium in shaking flask:

Seed medium:
 Glucose: 1.5 g/dl
 Ammonium acetate: 0.3 g/dl
 Urea: 0.1 g/dl
 $KH_2PO_4$: 0.1 g/dl
 $MgSO_4.7H_2O$: 0.04 g/dl
 $FeSO_4.7H_2O$: 1.0 mg/dl
 $MnSO_4.4H_2O$: 1.0 mg/dl
 Biotin: 50 μg/l
 Thiamine.HCl: 200 μg/l
 Soyprotein hydrolyzate (Total nitrogen 7%): 2.0 ml/dl
 pH 7.5

Cultivation was carried out at 31° C. for 18 hours with shaking.

The following culture medium was prepared and 300 ml batches of the culture medium put in 1 l fermentation vessel, and heated to sterilize.

Cultivation medium:
 Glucose: 2.0 g/dl
 Ammonium acetate: 0.5 g/dl
 Urea: 0.2 g/dl
 $KH_2PO_4$: 0.1 g/dl
 $MgSO_4.7H_2O$: 0.04 g/dl
 $Fe++$: 2.0 ppm
 $Mn++$: 2.0 ppm
 Biotine: 50 μg/l
 Thiamine.HCl: 50 μg/l
 Nicothin amide: 1.0 mg/l
 Soyprotein HCl-hydrolyzate (Total nitrogen 7%): 3.0 ml/dl
 pH 7.2

Each batch of the culture medium was inoculated with 15 ml of seed culture broth, and agitated and aerated. During the cultivation, a mixture solution of acetic acid and ammonium acetate was fed into the medium adjusting the pH to 7.2–8.0, and the temperature was held at 31°–33° C.

When the cultivation was continued for 55 hours, the amounts of L-lysine shown in Table 3 were accumulated.

TABLE 3

| Microorganism used | L-Lysine accumulated (g/dl) | Yield of L-lysine against consumed acetic acid (%) |
|---|---|---|
| AJ 11273 | 8.4 | 3.2 |
| AJ 11082 | 7.2 | 2.9 |

EXAMPLE 3

Brevibacterium lactofermentum AJ 11273 and AJ 11082 were cultured in 50 ml of the seed medium shown in Example 2 (ammonium acetate in the seed medium was replaced with 0.5 g/dl ethylalcohol, and the amount of urea was increased to 0.3 g/dl), at 31° C. for 18 hours.

Three hundreds ml batches of the culture medium shown in Example 2 (glucose concentration was decreased to 1 g/dl, ammonium acetate was replaced with 1 g/dl ethylalcohol and 0.5 g/dl ammonium sulfate was added to the culture medium) were placed in 1 l fermentation vessels, and heated to sterilize. Each bach was inoculated with 15 ml of the seed culture broth and held at 31°~33° C. with agitation and aeration. During the cultivation, the pH of the medium was adjusted to 7.2~8.2 with gaseous ammonia, and the ethylalcohol concentration was maintained at about 0.3% with feeding ethylalcohol.

After 48 hours of the cultivation, the amounts of L-lysine shown in Table 4 were found.

TABLE 4

| Microorganisms used | L-Lysine accumulated (g/dl) | Yield of L-lysine against ethylalcohol consumed (%) |
|---|---|---|
| AJ 11273 | 8.0 | 31 |
| AJ 11082 | 6.8 | 27 |

What is claimed is:
1. A method for producing L-lysine by fermentation which comprises culturing a mutant of the genus Brevibacterium or Corynebacterium in a culture medium until L-lysine is accumulated in the culture medium and recovering the L-lysine so accumulated, said mutant being sensitive to fluoropyruvic acid capable of producing L-lysine and being selected from the class consisting of *Brevibacterium lactofermentum* NRRL B-11471, *Corynebacterium acetoglutamicum* NRRL B-11473, and *Brevibacterium flavum* NRRL B-11475.

2. A method according to claim 1, wherein the L-lysine producing mutant is *Brevibacterium lactofermentum* NRRL B-11471.

3. A method according to claim 1, wherein the L-lysine producing mutant is *Corynebacterium acetoglutamicum* NRRL B-11473.

4. A method according to claim 1, wherein the L-lysine producing mutant is *Brevibacterium flavum* NRRL B-11475.

UNITED STATES PATENT AND TRADEMARK OFFICE
CERTIFICATE OF CORRECTION

PATENT NO. : 4,275,157
DATED : June 23, 1981
INVENTOR(S) : Tosaka, et. al.

It is certified that error appears in the above-indentified patent and that said Letters Patent is hereby corrected as shown below:

Column 2, line 14, replace "B-11475" with --B-11472--;

line 16, replace "B-11474" with --B-11475--;

line 17, replace "B-11472" with --B-11474--.

Signed and Sealed this

Sixth Day of May, 1997

*Attest:*

BRUCE LEHMAN

*Attesting Officer*     *Commissioner of Patents and Trademarks*